United States Patent [19]

Wong et al.

[11] Patent Number: 5,976,507

[45] Date of Patent: Nov. 2, 1999

[54] DENTRIFICE COMPOSITION CONTAINING ENCAPSULATED REACTIVE INGREDIENTS

[75] Inventors: Mike Wong, North Brunswick; Michael Prencipe, West Windsor, both of N.J.

[73] Assignee: Colgate Palmolive Company, New York, N.Y.

[21] Appl. No.: 09/090,293

[22] Filed: Jun. 4, 1998

[51] Int. Cl.$^6$ .............................. A61K 7/16; A61K 7/18; A61K 9/48

[52] U.S. Cl. ............................. 424/52; 424/49; 424/451; 424/494; 424/495

[58] Field of Search .......................................... 424/49–88

[56] References Cited

U.S. PATENT DOCUMENTS

| | | | |
|---|---|---|---|
| 3,929,988 | 12/1975 | Barth | 424/54 |
| 3,957,964 | 5/1976 | Grimm, III | 424/49 |
| 4,071,614 | 1/1978 | Grimm, III | 424/49 |
| 4,080,440 | 3/1978 | Di Guilio et al. | 424/49 |
| 4,083,955 | 4/1978 | Grabenstetter et al. | 424/49 |
| 4,397,837 | 8/1983 | Raaf et al. | 424/49 |
| 4,572,833 | 2/1986 | Pederson et al. | 424/20 |
| 4,923,683 | 5/1990 | Sakuma et al. | 424/52 |
| 5,472,712 | 12/1995 | Oshlack et al. | 424/480 |
| 5,571,502 | 11/1996 | Winston et al. | 424/52 |
| 5,603,922 | 2/1997 | Winston et al. | 424/49 |
| 5,614,175 | 3/1997 | Winston et al. | 424/52 |
| 5,645,853 | 7/1997 | Winston et al. | 424/440 |
| 5,695,784 | 12/1997 | Pollinger et al. | 424/495 |

*Primary Examiner*—Shep K. Rose
*Attorney, Agent, or Firm*—Paul Shapiro

[57] ABSTRACT

An aqueous dentifrice composition comprising an aqueous vehicle containing at least two active ingredients reactive with each other, at least one of the active ingredients being encapsulated in a substantially water immiscible, pressure rupturable shell which is rupturable during use of the dentifrice, causing the same to be released for interaction with the other active ingredient, the shell being formed from a plasticized alkyl cellulose polymer. The dentifrice exhibits increased efficacy for fluoridation of teeth when the active ingredients are soluble fluoride salt and a calcium salt encapsulated in the plasticized alkyl cellulose polymer.

12 Claims, No Drawings

DENTRIFICE COMPOSITION CONTAINING ENCAPSULATED REACTIVE INGREDIENTS

BACKGROUND OF THE INVENTION

1. Field of the Invention

This invention is directed to an aqueous dentifrice composition containing a plurality of reactive agents in which one of the agents is encapsulated in a pressure rupturable shell.

2. The Prior Art

It has long been known to include fluoride containing compounds in dentifrices as anticaries agents, and it has been established that these compounds are effective to reduce the incidence of dental caries. Fluoride compounds which are deemed to be the most effective are sodium fluoride, sodium monoflurophosphate and stannous fluoride. The fluoride compounds are effective mainly due to the fluoride ions which improve the acid resistance of tooth enamel and accelerate recalcification of decayed teeth in their early stage when the decalcification has proceeded only slightly. The effect of improving the acid resistance of the enamel is believed to be due to the fact that the fluoride ions are incorporated into a crystal lattice of hydroxyapatite which is the main constituent of tooth enamel or, in other words, fluoride ions partially fluoridate hydroxyapatite and simultaneously repair the lattice irregularities.

The effectiveness of fluoride treatment in providing acid resistance is dependent upon the amount of fluoride ion which is available for deposition on the enamel being treated. It is, therefore, desirable to formulate dentifrice compositions which provide maximum fluoride ion availability in brushing solutions formed using the dentifrice.

It is known to the art, e.g., U.S. Pat. No. 5,045,305, that an effective way of depositing fluoride on teeth is to use a two-component rinse composition to deposit freshly precipitated calcium fluoride on teeth in which one rinse solution contains $CaCl_2$ and the other contains fluoride ions in the form of NaF, the separate solutions being admixed immediately prior to introduction in the mouth, to effect interaction and rapid precipitation of $CaF_2$.

U.S. Pat. No. 5,145,668 discloses a method of fluoridating teeth wherein there is mixed in the mouth a first solution containing a soluble calcium salt such as $CaCl_2$ contained in a non-reactive vehicle and a second component containing a fluoride compound such as sodium fluorosilicate ($Na_2SiF_6$) contained in a non-reactive vehicle, the mixing of the components resulting in the precipitation of calcium fluoride and its deposition on tooth surfaces.

Although the methods disclosed in U.S. Pat. No. 5,045,305 and U.S. Pat. No. 5,145,668 are effective means to achieve fluoridation, the separate solutions containing calcium and fluoride salts must be mixed daily which is a time consuming daily chore. As a result, it is very difficult for the potential beneficiaries of such therapy to faithfully adhere to the regimen. However, simply combining the calcium and fluoride salts into a single formulation will not provide an effective means for fluoridation as the presence of the calcium salt removes soluble ionic fluoride from the dentifrice by forming insoluble and inactive calcium fluoride ($CaF_2$) thereby reducing the anticariogenic effectiveness of the fluoride dentifrice. Efforts to practice the methods disclosed in these U.S. patents using semi-solid, extrudable vehicle formulations such as toothpastes and gels have been unable to provide the theoretical maximum soluble fluoride because of the tendency for the ionic fluoride originally included in the dentifrice to be prematurely inactivated as the levels of the other conventional dentifrice composition ingredients such as antitartar pyrophosphate salts, antibacterial agents such as triclosan, abrasives such as dicalcium phosphate or silica are increased to that required in the semi-solid dentifrice.

Thus, there is a clear need to formulate a semi-solid dentifrice product such as a toothpaste or gel utilizing a fluoride compound or other active compound wherein the ingredients used to prepare the dentifrice vehicle do not interact with each other such as in the aforementioned inactivation of fluoride ion so that optimum uptake of fluoride is accomplished when the dentifrice is applied to the teeth. Moreover, it is desirable to include reactive compounds such as calcium and fluoride salts in a single highly stable dentifrice form which is susceptible to conventional packaging and dispensing systems and which can be readily and effectively used by the consumer.

The dentifrice art discloses several means to isolate active ingredients from interaction with other ingredients present in the dentifrice. For example, U.S. Pat. Nos. 3,957,964, 3,929,988, 4,071,614 and 4,348,378 disclose aqueous dentifrices containing ingredients such as flavors and dyes whereby such ingredients are encapsulated in rupturable, water-insoluble capsules so that the flavors and dyes are maintained substantially separate from other dentifrice ingredients during manufacture and storage, while subsequently being released when the dentifrice containing the encapsulated ingredients are applied topically to tooth surfaces, the mechanical agitation with a toothbrush rupturing the encapsulating shell whereby the encapsulated ingredient is released to the tooth surface. Materials from which the encapsulating shell is formed are diverse and include synthetic organic plastic materials such as phenol formaldehydes, vinyl chloride polymers, polyethylene, polypropylene, polyurethanes, ABS resins, waxes and cellulosic materials such as ethyl cellulose, butyl cellulose and nitrocellulose.

U.S. Pat. No. 4,837,008 discloses incorporating both bicarbonate and peroxide salts in a non-aqueous dentifrice vehicle whereby interaction between the two salts are prevented by providing at least one of the salts with a water soluble barrier coating of a non-toxic polymer or gum such as a cellulosic polymer or guar gum whereby the salts are released in the aqueous environment of the mouth when the dentifrice is applied to the teeth.

Although the coatings and encapsulants materials of the prior art are effective to some degree to prevent interaction between active compounds such as soluble fluoride with other dentifrice ingredients, it has been determined that such materials are inadequate to fully prevent interaction due to premature leakage of soluble reactive salts from the coating and encapsulating materials whereby, as the case of fluoride salts, there results a significant loss of ionic fluoride and reduced levels of soluble fluoride availability in the dentifrice compositions stored for prolonged period of time.

SUMMARY OF THE INVENTION

In accordance with the present invention there is provided an aqueous dentifrice composition wherein the dentifrice is prepared using an aqueous vehicle containing at least two active compounds which are reactive with each other, wherein at least one of the active compounds is encapsulated in a water-insoluble, pressure rupturable shell formed from a substantially water impermeable plasticized alkyl cellulose polymer which shell is rupturable during use of the dentifrice causing the encapsulated compound to be released for interaction with the other active compounds present in the dentifrice composition when a portion of the dentifrice composition is applied to and brushed on the teeth, the brushing causing the rupture of the capsules whereby the encapsulated ingredient is released for access to tooth surfaces.

DESCRIPTION OF THE PREFERRED EMBODIMENTS

The term n"capsule" as used herein means a core material such as a salt or other compound which releases reactive ions which compound is isolated from the surrounding environment by a protective coating or shell which subsequently releases the core compound, that is, ruptures, in response to forces exerted on the capsule upon use, as in brushing the teeth with the dentifrice in which the capsule is incorporated. In the practice of the present invention, the core compound comprises about 40 to about 70% by weight of the capsule and the shell material encapsuating the core compound comprises about 30 to about 60% by weight of the capsule.

The encapsulation material used to prepare the water impermeable capsules of the present invention is a substantially water-insoluble plasticized film forming alkyl cellulosic polymer material. The terin alkyl cellulosic polymer includes within its meaning methyl cellulose, ethyl cellulose, hydroxyethylcellulose, and hydropropyl methyl cellulose. As will hereinafter be demonstrated, it is critical to the practice of the present invention that the water-insoluble alkyl cellulosic polymer film forming material have incorporated therein a plasticizer.

A commercially available plasticized alkyl cellulose polymer encapsulation material preferred in the practice of the present invention is Aquacoat®, available from FMC Corporation, Philadelphia, Pa., U.S.A., which is an aqueous dispersion of ethylcellulose to which a plasticizer has been added. U.S. Pat. No. 5,500,227 discloses that Aquacoat is prepared by dissolving the ethyl cellulose in a water immiscible organic solvent and then emulsifying the same in water in the presence of a surfactant such as sodium lauryl sulfate. After homogenization to generate submicron droplets, the organic solvent is evaporated under vacuum to form a pseudolatex. Thereafter a plasticizer is intimately mixed with the pseudolatex to prepare the shell forming material. The plasticizer is added to the pseudolatex at a solids concentration of about 1.5 to 3.5% by weight and preferably about 2.5 to about 2.7% by weight, the balance being water and a minor amount of surfactant generally about 0.5 to about 2% by weight. During the process by which the reactive ingredient is encapsulated, the water is removed whereby the solid shell forming encapsulating material that remains is comprised of about 80 to about 90% by weight of the alkyl cellulose polymer, about 7 to about 10% by weight of the plasticizer and about 3–5% by weight of the surfactant. It is critical to the practice of the present invention, that the plasticized alkyl cellulose polymer solids content included in the shell forming dispersion be at a concentration of at least about 30% by weight and preferably 30 to about 60% by weight. When lower plasticized alkyl cellulose solids concentrations are used to prepare the encapsulant shells, leakage of core ingredients from the capsule is observed.

Exemplary plasticizers suitable for use in combination with the alkyl cellulose polymer to prepare the shell forming material are described in U.S. Pat. No. 5,536,507 and include triacetin, acetyl tributyl citrate, diethyl sebacetate, triethyl citrate available from Morflex Company under the trademark Citroflex 2, dibutyl sebacetate, dibutyl succinate, diethyl phthalate and acetylated monoglycerides available commercially from Eastman Chemical Company under the trade designation Myvacet-9-40.

Generally known encapsulation processes can be used to prepare the capsules of the present invention, but a preferred method is spray drying wherein the solid core material to be encapsulated, such as calcium acetate, is dispersed and suspended in a reactor by a continuous stream of heated air at a flow rate of about 500 to 2000 cubic meters for about 5 to 60 minutes. The shell forming material is then sprayed through a nozzle of the desired particle size onto the air-suspended core material. During the formation of the capsules, water is flashed off by the heated air. The particle size and amount of encapsulant material is controlled by spray time and air flow. The particle size of the resultant encapsulated core material ranges from 1 to 1000 microns, preferably 5 to 50 microns.

The dentifrice composition of the present invention is prepared in the form of a semi-solid product of desired consistency which is extrudable from a pump or collapsible tube. In general, the liquids that form the dentifrice vehicle will comprise water, in an amount ranging from about 5 to abut 30% by weight and preferably about 5 to about 20% by weight and a humectant such as glycerin, sorbitol polyethylene glycol or a mixture thereof in an amount greater than about 35% by weight and preferably about 50 to about 70% by weight.

In the preparation of dentifrices to be used for the fluoridation of teeth, suitable fluoride salts useful as fluoridation agents include alkali metal fluoride salts such as sodium fluoride, sodium monofluorophosphate and tin salts such as stannous fluoride. The fluoride salt is incorporated in the dentifrice composition at a concentration of about 0.1 to about 1% by weight, and preferably at about 0.25 to about 0.5% by weight. At these preferred concentrations, about 500 ppm to about 2200 ppm, fluoride ion will be available to teeth when the dentifrice composition is applied to the teeth.

Surfactants are used in the compositions of the present invention to achieve increased prophylactic action and render the dentifrice compositions more cosmetically acceptable. The surfactant is preferably a detersive material which imparts to the composition detersive and foaming properties. Suitable examples of surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, sodium lauryl sulfoacetate and higher fatty acid esters of 1,2-dihydroxy propane sulfonate. The surfactant is typically present in the dentifrice compositions of the present invention in an amount of about 0.3 to about 5% by weight, preferably about 0.5 to about 2% by weight.

Thickening agents commonly used as dentifrice thickening agents such as guar gum, carboxymethyl cellulose and polyoxyethylene polyoxypropylene glycol block copolymers and xanthan gum are used at a concentration of about 0.5 to about 2% in the preparation of the dentifrice composition of the present invention which amount is sufficient to form of a semi-solid, extrudable, shape retaining product.

In the preparation of dentifrices which are to be used for the fluoridation of teeth, agents which interact with fluoride ions which are included in the dentifrice composition of the present invention are maintained physically isolated from the fluoride ingredient by their encapsulation in a shell of the plasticized alkyl cellulose polymer. To obtain freshly precipitated calcium fluoride upon brushing teeth with the dentifrice composition, there is included in the dentifrice composition a water soluble calcium salt such as calcium chloride, calcium acetate, calcium butylate, calcium citrate, calcium lactate, calcium salicylate, and other non-toxic salts of calcium and inorganic or organic acids which are soluble in an aqueous media and are present in the dentifrice at a level required for substantial interaction with the fluoride compound to deposit $CaF_2$ during the time the dentifrice is applied to the teeth and brushed.

The encapsulated calcium ion releasable salt is incorporated in the dentifrice composition of the present invention at a concentration of about 0.1% to about 5% by weight and preferably at about 0.5 to about 1.5% by weight.

Other fluoride ion inactivating ingredients conventionally present in dentifrice compositions which may be encapsulated and used in the practice of the present invention, include abrasives such as silica, calcium carbonate and dicalcium phosphate (anhydrous and/or dihydrate). Abrasives such as silica have very large surface areas whereby fluoride ion may be lost to the silica abrasive through chemisorption. Calcium containing abrasives, although substantially water insoluble, will nonetheless release amounts of calcium ion in sufficient amounts to interact and thereby inactivate fluoride ion present in the dentifrice.

An abrasive is generally included in the dentifrice composition of the present invention at a concentration of about 10 to about 30% by weight and preferably at a concentration of about 15 to about 25% by weight. Soluble abrasives include precipitated amorphous hydrated silica, such as Sorbosil AC-35 marketed by Crosfield Chemicals, or Zeodent 115 from J.M. Huber Company, sodium metaphosphate, potassium metaphosphate, tricalcium phosphate, calcium phosphate dihydrate, anhydrous dicalcium phosphate, calcium pyrophosphate, sodium bicarbonate, calcium carbonate and calcined alumina.

In addition to abrasive materials being incompatible with fluoride salts, it has been further determined that pyrophosphate salts, normally included in dentifrice compositions as antitartar agents, have also been determined to inactivate fluoride ion so it is desirable that these salts be encapsulated in accordance with the practice of the present invention. Exemplary antitartar pyrophosphate salts include dialkali or tetraalkali metal pyrophosphate salts such as $Na_4P_2O_7$, $K_4P_2O_7$, $Na_4K_2P_2O_7$, $Na_4H_2P_2O_7$ and $K_2H_2P_2O_7$ long chain polyphosphates such as sodium hexametaphosphate, sodium tripolyphosphate and cyclic phosphates such as sodium trimetaphosphate. These salts are included in the dentifrice composition of the present invention at a concentration of about 1 to about 7% by weight.

Synthetic anionic polycarboxylates may also be used in the dentifrice compositions of the present invention to enhance the efficacy of other active agents present in the dentifrice such as antibacterial agents and the antitartar pyrophosphate salts. Such anionic polycarboxylates are generally employed in the form of their free acids or preferably partially or more preferably fully neutralized water soluble alkali metal, e.g., potassium and preferably sodium or ammonium salts. Preferred polycarboxylate compounds are 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000 most preferably about 30,000 to about 500,000. These copolymers are commercially available, for example, under the trade designation, as Gantrez, e.g. AN 139 (M.W. 500,000), AN 119 (M.W. 250,000); and preferably S-97 Pharmaceutical Grade (M.W. 70,000). The synthetic anionic carboxylates may be included in the dentifrice composition of the present invention at a concentration of about 0.5 to about 5% by weight.

The dentifrice composition of the present invention may also contain a flavoring agent. The flavoring agent is incorporated in the dentifrice composition at a concentration of about 0.1 to about 5% by weight and preferably about 0.5 to about 1.5% by weight. Flavoring agents which are used in the practice of the present invention include essential oils as well as various flavoring aldehydes, esters, alcohols, and similar materials. Examples of the essential oils include oils of spearmint, peppermint, wintergreen, sassafras clove, sage, eucalyptus, marjoram, cinnamon, lemon, lime, grapefruit, and orange. Of these, the most commonly employed are the oils of peppermint and spearmint.

Various other materials may be incorporated in the dentifrice compositions of this invention, including antibacterial agents such as Triclosan, chlorhexidine, desensitizers such as potassium nitrate, and potassium citrate, whitening agents such as hydrogen peroxide, calcium peroxide and urea peroxide, preservatives, silicones, and chlorophyll compounds. These adjuvants, when present, may also be encapsulated when they are incorporated in the dentifrice composition in amounts which are reactive with other dentifrice ingredients such as fluoride salts.

The preparation of dentifrice compositions is well known in the art. U.S. Pat. Nos. 3,996,863, 3,980,767, 4,328,205 and 4,358,437, which are incorporated herein by reference, describe toothpastes and methods of production thereof which may be utilized for production of the dentifrices of the present invention.

The following example is illustrative of the subject invention, and does not limit it. All parts or percentages are by weight and all temperatures are in degrees C., unless specifically stated to be otherwise.

EXAMPLE I

Calcium acetate particles were encapsulated in a plasticized ethyl cellulose shell by dispersing and suspending the calcium acetate particles in a reactor vessel under a continuous stream of heated air. An aqueous dispersion containing 30% by weight ethyl cellulose, 3% triethylcitrate, 1.2% by weight sodium lauryl sulfate and 65.8% water was sprayed into the air suspended calcium acetate particles at an air flow rate of 750–2000 cubic meters per/hour for about 28 minutes to prepare encapsulated calcium acetate particles having a particle size distribution of 5 to 20 microns.

The encapsulated calcium acetate particles were incorporated in a dentifrice composition having the ingredients listed in Table I below. Calcium ion analysis of the capsules did not detect surface calcium indicating that a continuous surface film had been applied.

TABLE I

| Ingredient | Weight % |
| --- | --- |
| Sorbitol (70%) | 60.77 |
| Polyethylene glycol 600 | 3.0 |

TABLE I-continued

| Ingredient | Weight % |
| --- | --- |
| Carboxymethyl cellulose | 0.60 |
| Sodium saccharin | 0.30 |
| Water, deionized | 6.44 |
| Zeodent 115 | 25.50 |
| Sodium fluoride | 0.243 (1100 ppm) |
| Flavor | 0.72 |
| Sodium lauryl sulfate | 1.2 |
| Encapsulated calcium acetate | 0.57 |
| Tetrasodium pyrophosphate | 0.5 |
| FDC Blue 1 (1% dye soln.) | 0.16 |

The dentifrice of Table I (designated "Example I") was packaged in sealed plastic toothpaste tubes and aged for six weeks at 50° C. in an air oven. Fluoride ion analysis of the aged dentifrice indicated 1050 ppm fluoride present evidencing minimal fluoride ion loss from the dentifrice, the shell having remained substantially intact after processing and aging.

To determine the rate of calcium release on brushing the Example I dentifrice was slurried (1:3 in water) and brushed in a trough for various time periods. The slurry contents were centrifuged and the supernatant analyzed for the presence of calcium ion.

The results are recorded in Table II below. For purposes of comparison, the procedure was repeated except the calcium acetate incorporated in the dentifrice was not encapsulated. The comparative dentifrice was designated "Control".

TABLE II

| Dentifrice Composition | Brushing Time (min.) | $Ca^{++}$ (ppm) |
| --- | --- | --- |
| Example I | 0.5 | 55 |
|  | 1.0 | 195 |
|  | 2.0 | 300 |
|  | 5.0 | 395 |
| Control | 0.5 | 550 |
|  | 1.0 | 900 |
|  | 2.0 | 990 |
|  | 5.0 | 1000 |

The results recorded in Table II indicates substantial amounts of the encapsulated calcium ion were released during brushing.

The degree of fluoride uptake on hydroxapatite disks (chemically similar to tooth enamel) was determined for the Example I dentifrice and for comparative purposes, the same dentifrice was prepared and evaluated for fluoride uptake except that the encapsulated calcium acetate ingredient was not present, the comparative dentifrice being identified as Composition "C". A slurry (1:3 in water) of these dentifrices was brushed for 30 seconds in a trough. The brushed slurry was centrifuged and the supernatant collected. The hydroxyapatite (HAP) disks were exposed to the slurry for 5 minutes each time for a total of 10 exposures. The disks were then dipped into perchloric acid for 60 seconds to remove the surface layer containing the fluoride and then analyzed for fluoride ion content. The results are recorded in Table III below.

TABLE III

| Dentifrice Composition | Fluoride uptake on HAP disks |
| --- | --- |
| Example 1 | 0.305 +/− 0.010 |
| C | 0.07 +/− 0.005 |

The results show that the disks that were exposed to the Example I dentifrice containing both encapsulated calcium acetate and sodium fluoride showed a substantial and significant increase in fluoride uptake as compared to the comparative dentifrice (C) which did not contain calcium acetate.

EXAMPLE II

The procedure of Example I was repeated except that for purposes of comparison the following dispersions containing a series of comparative encapsulating materials listed in Table IV were used to prepare calcium acetate capsules:

TABLE IV

| Capsule Composition | Dispersion Solids Content (Wt. %) | Encapsulant Material |
| --- | --- | --- |
| $C_1$ | 30% | non-plasticized ethylcellulose |
| $C_2$ | 5% | plasticized ethyl cellulose |
| $C_3$ | 30% | vegetable |
| $C_4$ (control) | — | None |

Dentifrice compositions containing the comparative calcium acetate capsules were prepared following the procedure of Example I and were packaged in sealed plastic toothpaste tubes and aged at 120° F. for a six week period. The fluoride availability of the aged dentifrices is recorded in Table V below.

TABLE V

| Dentifrice Composition | Fluoride Availability (ppm) | | | |
| --- | --- | --- | --- | --- |
|  | Initial 72° F. | 2 weeks @ 120° F. | 4 weeks @ 120° F. | 6 weeks @ 120° F. |
| Example 1 | 1000 | 1000 | 985 | 975 |
| $C_1$ | 1000 | 890 | 422 | 119 |
| $C_2$ | 20 | 0 | 0 | 0 |
| $C_3$ | 1000 | 695 | 210 | 55 |
| $C_4$ | 10 | 0 | 0 | 0 |

The data recorded in Table V show that over the 6 week aging period there was no meaningful loss of fluoride availability in the dentifrice of the present invention which contained calcium acetate encapsulated in a shell of plasticized ethyl cellulose (Example I), whereas there was substantially complete loss of fluoride availability in dentifrices in which the encapsulant material was (1) non-plasticized ethyl cellulose (Composition $C_1$), (2) the encapsulant was a plasticized ethylcellulose in which the solids content in the dispersion was less than 30% by weight (Composition $C_2$) or (3) the encapsulant was a non-alkyl cellulose polymer encapsulant such as vegetable wax (Composition $C_3$).

What is claimed is:

1. An aqueous dentifrice composition comprising an aqueous vehicle containing at least two active compounds which are reactive with each other, at least one of the active ingredients is a calcium salt or fluoride salt contained in a capsule which is comprised of one of said two actives as a core active compound, which is encapsulated in a substantially water impermeable, shell material rupturable during use of the dentifrice whereby the core compound is released for interaction with the other active compound, the shell being formed from a plasticized alkyl cellulose polymer.

2. The composition of claim 1 wherein the alkyl cellulose polymer is ethyl cellulose.

3. The composition of claim 1 wherein the ethyl cellulose is plasticized with triethylcitrate.

4. The composition of claim 1 wherein the capsule is comprised of about 40 to about 70% by weight of the reactive ingredient and about 30 to about 60% by weight of the plasticized alkyl cellulose polymer shell material.

5. The composition of claim 1 wherein the encapsulated compound is a soluble calcium salt and the other compound is a fluoride salt.

6. A method for applying therapeutic agents to teeth comprising preparing a dentifrice comprised of a dentifrice comprised of an aqueous vehicle containing a water soluble therapeutic agent calcium or fluoride salt and a capsule which comprises a core ingredient reactive with therapeutic agent, the core ingredient being a calcium or fluoride salt encapsulated in a substantially water impermeable, shell material rupturable during use of the dentifrice, applying the dentifrice to the teeth with sufficient force to cause the release of the reactive ingredient from the capsule for interaction with the therapeutic, the shell being formed from a plasticized alkyl cellulose polymer.

7. The method of claim 6 wherein the alkyl cellulose polymer is ethyl cellulose.

8. The method of claim 6 wherein the alkyl cellulose polymer is plasticized with triethylcitrate.

9. The method of claim 6 wherein the capsule is comprised of about 40 to about 70% by weight of the reactive ingredient and about 30 to about 60% by weight of the plasticized alkyl cellulose polymer shell material.

10. The method of claim 7 wherein the therapeutic agent is a water soluble fluoride ion releasable salt and the core ingredient is a water soluble calcium salt.

11. An aqueous dentifrice composition comprising an aqueous vehicle containing at least two active compounds which are reactive with each other, one of which is a water soluble calcium salt and the other is a water fluoride salt, at least one of the active compounds is encapsulated in a substantially water impermeable, shell material rupturable during use of the dentifrice whereby the encapsulated active compound is released for interaction with the other active compound, the shell being formed from a plasticized alkyl cellulose polymer prepared from an aqueous dispersion of a plasticized alkyl cellulose polymer containing about 30 to about 60% by weight of shell forming solids comprised of about 80 to 90% of the alkyl cellulose polymer, about 7 to about 10% by weight of the plasticizer and about 3 to about 5% by weight of a surfactant.

12. A method for applying therapeutic agents to teeth comprising preparing a dentifrice comprised of a dentifrice comprised of an aqueous vehicle containing a water soluble fluoride salt and a capsule which comprises a water soluble calcium salt reactive with the fluoride salt, the calcium salt being encapsulated in a substantially water impermeable, shell material rupturable during use of the dentifrice, applying the dentifrice to the teeth with sufficient force to cause the release of the calcium salt from the capsule for interaction with the fluoride salt, the shell being formed from an aqueous dispersion of a plasticized alkyl cellulose polymer having dispersed therein about 30 to about 60% by weight of shell forming solids comprised of about 80 to 90% of the alkyl cellulose polymer, about 7 to about 10% by weight of the plasticizer and about 3 to about 5% by weight of a surfactant.

* * * * *